US009144642B2

(12) United States Patent
Hwang et al.

(10) Patent No.: US 9,144,642 B2
(45) Date of Patent: Sep. 29, 2015

(54) SHIPPING CONTAINER INTEGRATING A SHARPS DISPOSAL CONTAINER WITH A NEW PRODUCT STORAGE CONTAINER

(75) Inventors: Charles G. Hwang, Wellesley, MA (US); Joshua D. Horvath, Sparta, NJ (US); Christopher Schlenk, Morristown, NJ (US); Roman Tunkel, Arlington, MA (US); Zenia Zaveri, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1331 days.

(21) Appl. No.: 12/563,090

(22) Filed: Sep. 18, 2009

(65) Prior Publication Data

US 2011/0068034 A1   Mar. 24, 2011

(51) Int. Cl.
*A45F 4/02*   (2006.01)
*A61M 5/00*   (2006.01)
*A61B 19/02*   (2006.01)
*A61M 5/32*   (2006.01)
*B65D 6/00*   (2006.01)

(52) U.S. Cl.
CPC ............ *A61M 5/002* (2013.01); *A61B 19/0288* (2013.01); *A61M 5/3205* (2013.01); *B65D 11/10* (2013.01); *A61B 2019/0267* (2013.01); *B65D 2209/00* (2013.01)

(58) Field of Classification Search
CPC ......... B65F 1/163; B65F 1/08; B05B 7/2408; B05B 7/2478; B01L 3/5082
USPC ............ 220/23.83, 23.87; 206/204, 363, 366, 206/370, 386, 443, 505, 521.1, 600; 222/183, 494, 81; 229/104, 109, 110, 229/114, 117.02, 117.13, 117.27
See application file for complete search history.

(56) References Cited

U.S. PATENT DOCUMENTS 2,946,494 A * 7/1960 Kuss ........................ 229/117.3
4,576,281 A * 3/1986 Kirksey ...................... 206/370
4,722,472 A * 2/1988 Bruno ......................... 229/128
5,167,193 A * 12/1992 Withers et al. ............... 110/346

(Continued)

FOREIGN PATENT DOCUMENTS

EP   1 449 491 A1   8/2004
JP   61125970         8/1986

(Continued)

OTHER PUBLICATIONS

European Patent Office Communication Issued in Application No. 10 176 458.7-1662 dated Aug. 23, 2013.

(Continued)

*Primary Examiner* — Fenn Mathew
*Assistant Examiner* — Cynthia Collado
(74) *Attorney, Agent, or Firm* — Roylance, Abrams, Berdo & Goodman, LLP

(57) ABSTRACT

A shipping container integrates a sharps disposal container with a new product storage container for shipping. The storage container stores new product. A sharps disposal container receives used sharps. One of the storage container and the sharps disposal container is disposed within the other of the storage container and the sharps disposal container for shipping. A lid is adapted to be connected to the outermost container of the sharps disposal container and the storage container for shipping and to a top of the sharps disposal container for receiving used sharps.

12 Claims, 6 Drawing Sheets

(56) References Cited

U.S. PATENT DOCUMENTS

| | | | |
|---|---|---|---|
| 5,201,418 A * | 4/1993 | Hanlon | 206/366 |
| 5,427,238 A | 6/1995 | Weiss | |
| 7,021,463 B2 | 4/2006 | Phan | |
| 8,783,453 B2 | 7/2014 | Short | |
| 2006/0180643 A1* | 8/2006 | Stephenson | 229/117.3 |
| 2006/0229562 A1 | 10/2006 | Marsh et al. | |
| 2006/0243618 A1 | 11/2006 | Brown | |

FOREIGN PATENT DOCUMENTS

| | | |
|---|---|---|
| JP | 372506 | 7/1991 |
| JP | 7500753 A | 1/1995 |
| JP | 2002535035 A | 10/2002 |
| JP | 2008539871 A | 11/2008 |
| JP | 2009112805 A | 5/2009 |
| JP | 2009113865 A | 5/2009 |
| JP | 49-99624 B2 | 5/2012 |
| WO | 94/24021 A1 | 10/1994 |
| WO | 96/31414 A1 | 10/1996 |
| WO | 2010/042679 A1 | 4/2010 |

OTHER PUBLICATIONS

"Safe Disposal Options for Needles and Syringes" w-hhw4-67, Apr. 2008.

* cited by examiner

SHIPPING CONTAINER INTEGRATING A SHARPS DISPOSAL CONTAINER WITH A NEW PRODUCT STORAGE CONTAINER

FIELD OF THE INVENTION

The present invention relates to a shipping container that integrates a sharps disposal container with a new product storage container. More particularly, the present invention relates to a shipping container in which one of a new product container and a sharps disposal container is disposed inside the other. Still more particularly, the present invention relates to a shipping container in which a sharps disposal container has a movable portion that expands as new product is removed from a storage container in which the sharps disposal container is stored.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer.

The assembly and operation of a typical pen injection device, as shown in FIGS. 1 and 2, is described in U.S. Patent Application Publication No. 2006/0229562, published on Oct. 12, 2006, which is hereby incorporated by reference in its entirety.

Pen injection devices, such as the exemplary pen injector 100, as shown in FIG. 1, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location.

FIG. 2 is an exploded view of an exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer shield 69, which attaches to the hub 20, covers the hub. An inner shield 59 covers the patient needle 11 within the outer shield 69. The inner shield 59 can be secured to the hub 20 to cover the patient needle 11 by any suitable means, such as an interference fit or a snap fit. The outer shield 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

Following an injection, the used needle 11 and hub assembly 20, or "sharps", is removed and must be properly disposed of. Used sharps may become contaminated by body fluids and the like creating a hazard for anyone that may handle them following their use. Sharps disposal containers store the disposed sharps and prevent unintentional contact with any object disposed therein.

One problem associated with shipping new product and a sharps disposal container is that the new product and the sharps disposal container are each contained in separate rigid containers, such that the overall size of the shipping container is the size of both containers combined. Accordingly, a need exists for a shipping container that integrates a sharps disposal container with a new product storage container such that the size of the shipping container is substantially the same size as the larger of the storage container or the sharps disposal container.

SUMMARY OF THE INVENTION

In accordance with an aspect of the present invention, the shipping container integrates a sharps disposal container with a storage container containing new product such that one container is disposed inside the other for shipping.

In accordance with another aspect of the present invention, a storage container containing new product is disposed within a sharps disposal container for shipping, thereby reducing the size of the shipping container.

In accordance with yet another aspect of the present invention, a sharps disposal container having a movable partition is disposed within a storage container for shipping, thereby reducing the size of the shipping container.

The shipping container of an exemplary embodiment of the present invention integrates a disposal container with a new product storage container for shipping. The storage container stores new product. A disposal container receives used product, such as used sharps. One of the storage container and the disposal container is nested within the other of the storage container and the disposal container for shipping. A lid is adapted to be connected to the outermost one of the disposal container and the storage container for shipping and to a top of the disposal container for receiving the used product. Accordingly, a shipping container is provided that is not significantly larger than required to store the new product.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

Figure 1:
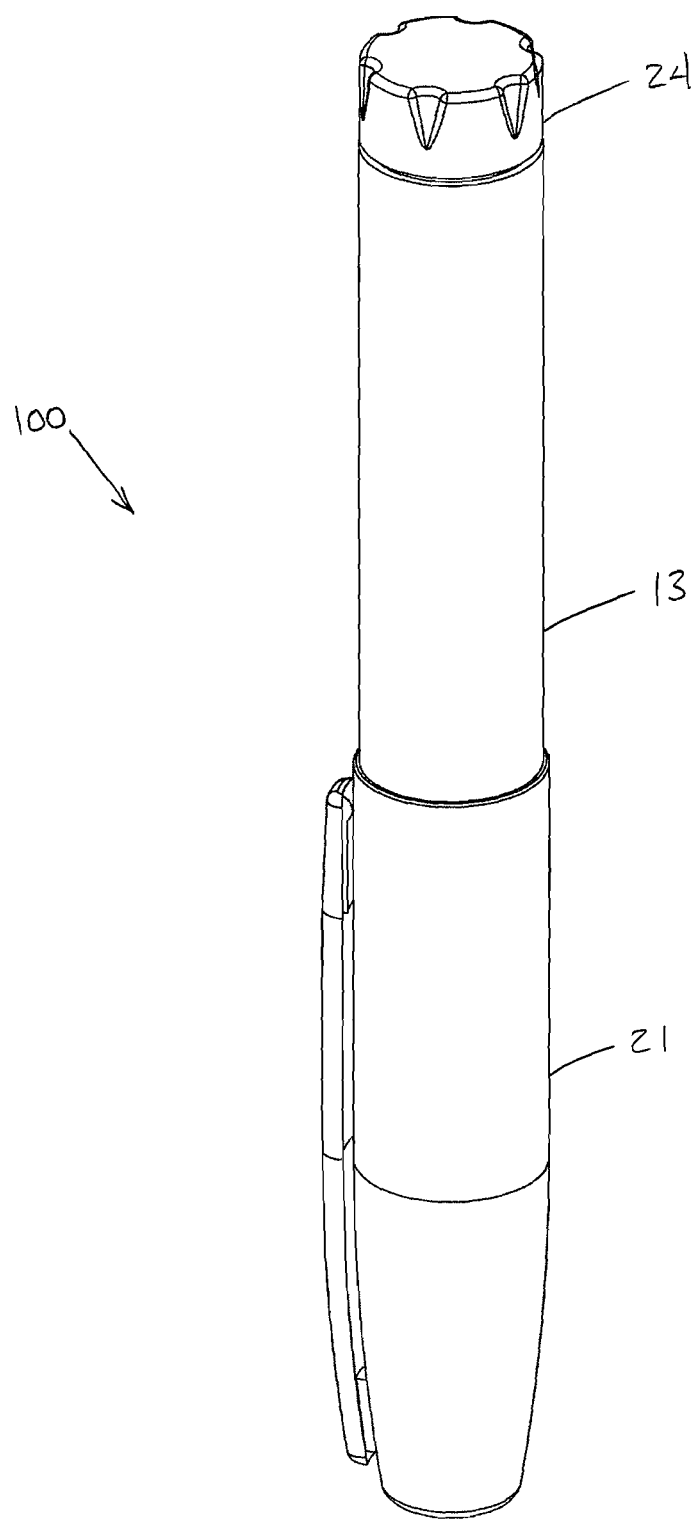
FIG. 1 is a perspective view of an assembled existing pen needle assembly.
Figure 2:
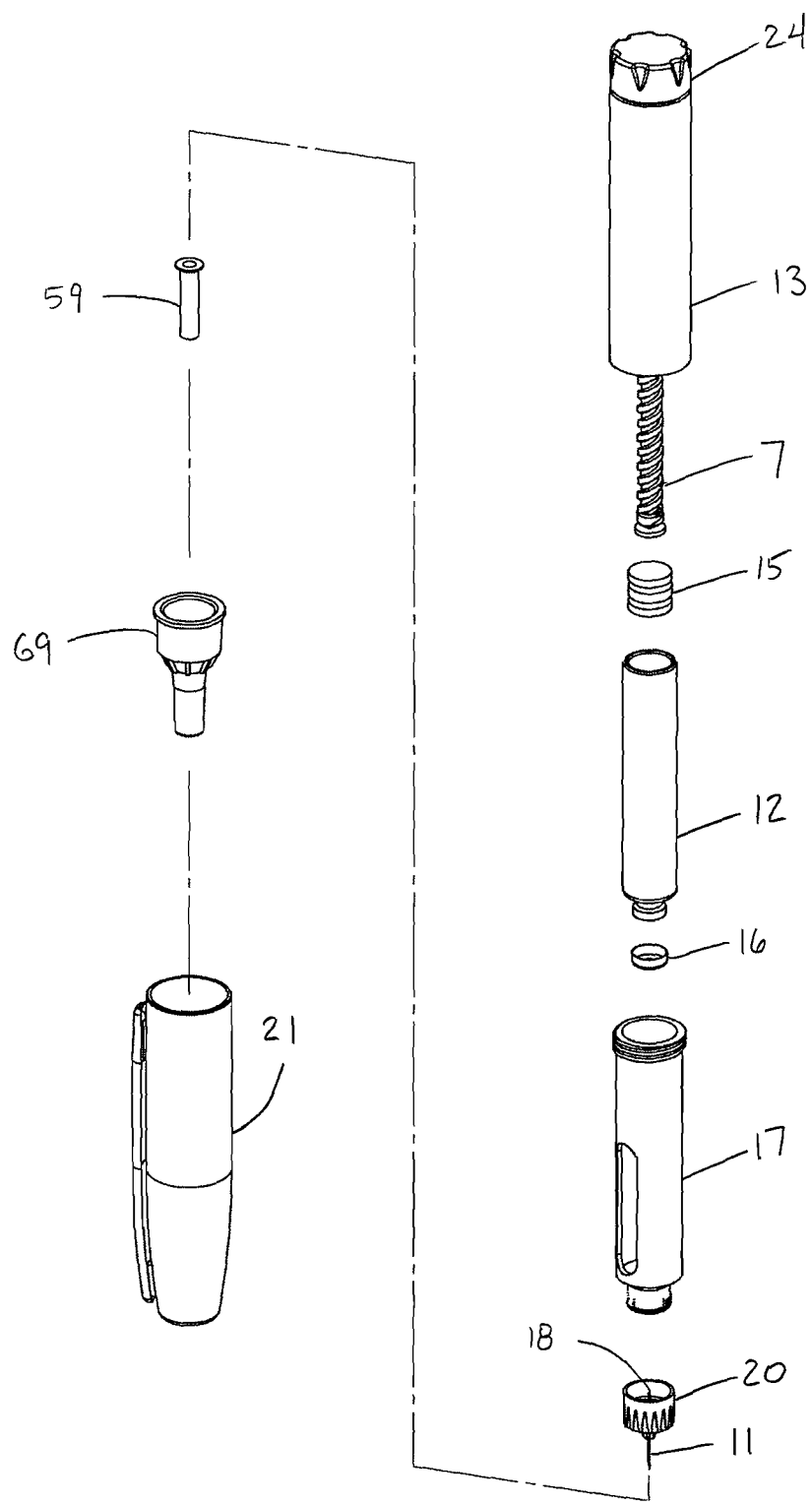
FIG. 2 is an exploded perspective view of the components of the pen needle assembly of FIG. 1.
Figures 3, 4:
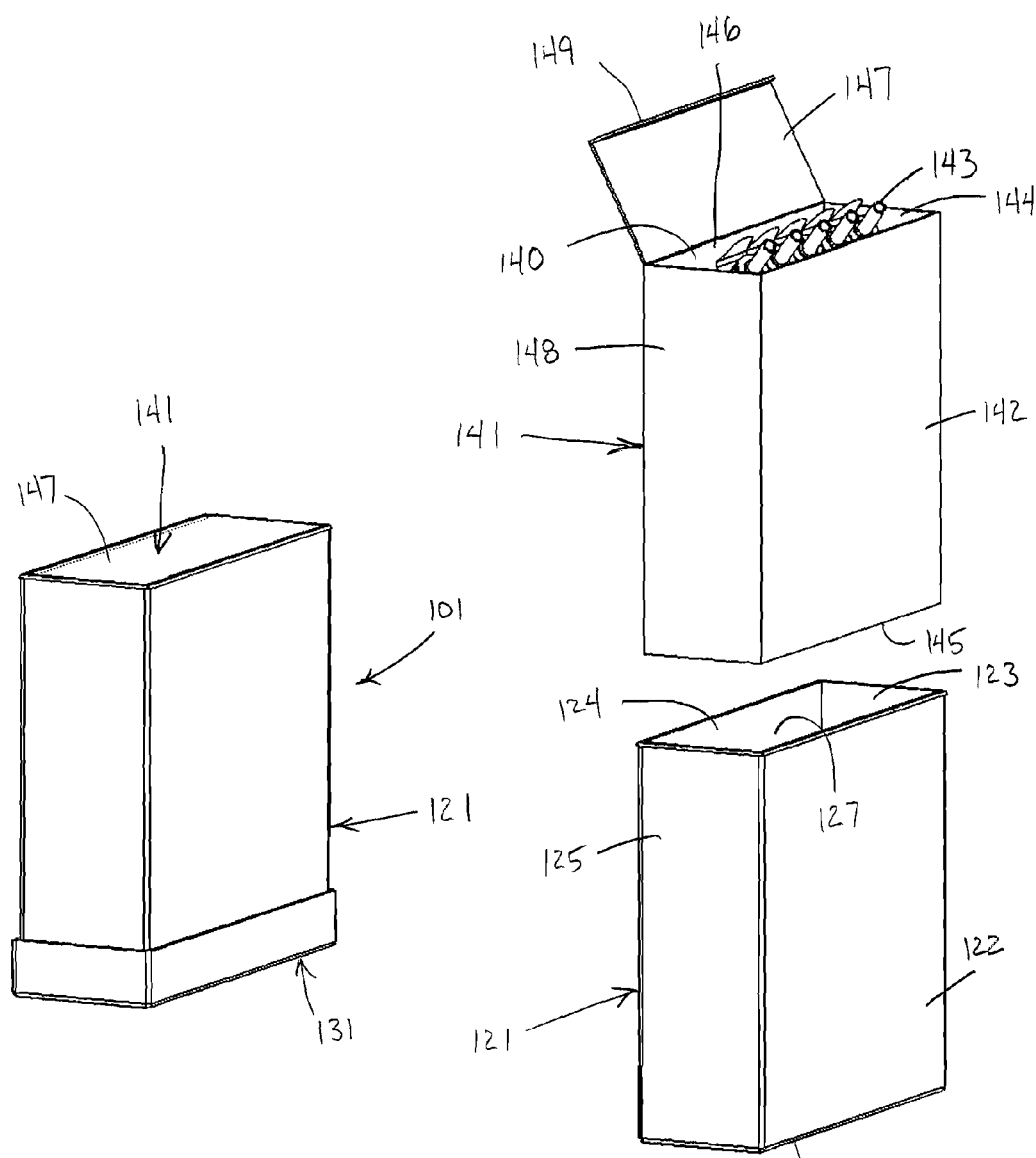
FIG. 3 is a perspective view of a sharps container according to an exemplary embodiment of the present invention.
FIG. 4 is an exploded perspective view of the sharps container of FIG. 3.

In an exemplary embodiment of the present invention, as shown in FIGS. 3-6, a shipping container 101 includes a storage container 141 containing new product, a sharps disposal container 121 for receiving used sharps, and a lid 131 for the sharps disposal container. As shown in FIG. 3, the storage container 141 is nested within the sharps disposal container 121, thereby creating a shipping container 101 that is substantially the same size as the sharps disposal container.

The storage container 141 contains new product 143, such as pen needle assemblies, as shown in FIG. 4. The storage container 141 has side walls 142, 144, 146 and 148 extending between a bottom wall 145 and a top wall 147, which has a flap 149. The top wall 147 is pivotally connected to side wall 146 such that the top wall 147 is movable to a position substantially parallel to the bottom wall 145, thereby allowing access to an internal volume 140 defined by the walls 142, 144 and 145-148. When the top wall 147 is substantially parallel to the bottom wall 145, the flap 149 is received within the internal volume 140 to provide a sealed container. The storage container 141 may be made of any suitable material, such as paperboard or cardboard. The new product is stored within the sealed container in any suitable manner, such as in a cardboard box, plastic bag or foil pouch, for shipping.

The sharps disposal container 121 has side walls 122-125 extending upwardly from a bottom wall 126. The walls 122-126 define an internal volume 127 that is open at the top and is adapted to receive used sharps.

Figure 6:
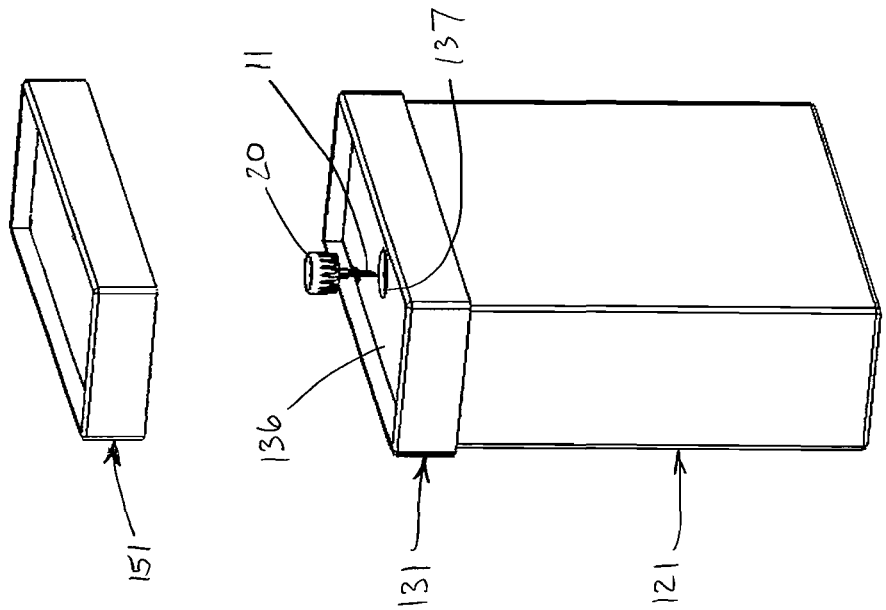
FIG. 6 is a perspective view of the sharps container in which the lid is disposed on top of the container.
Figure 5:
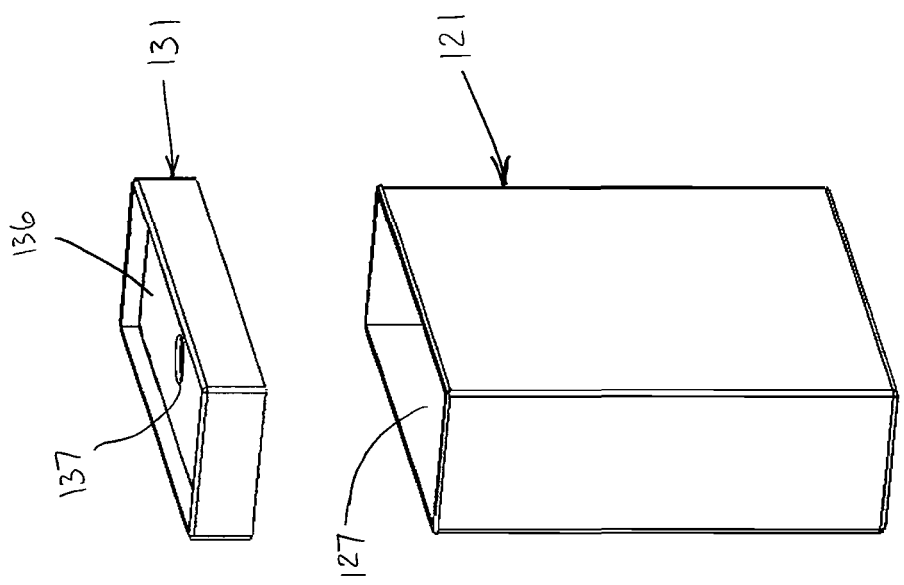
FIG. 5 is an exploded perspective view of the sharps container of FIG. 3 in which the lid is removed from the base.
Figure 7:
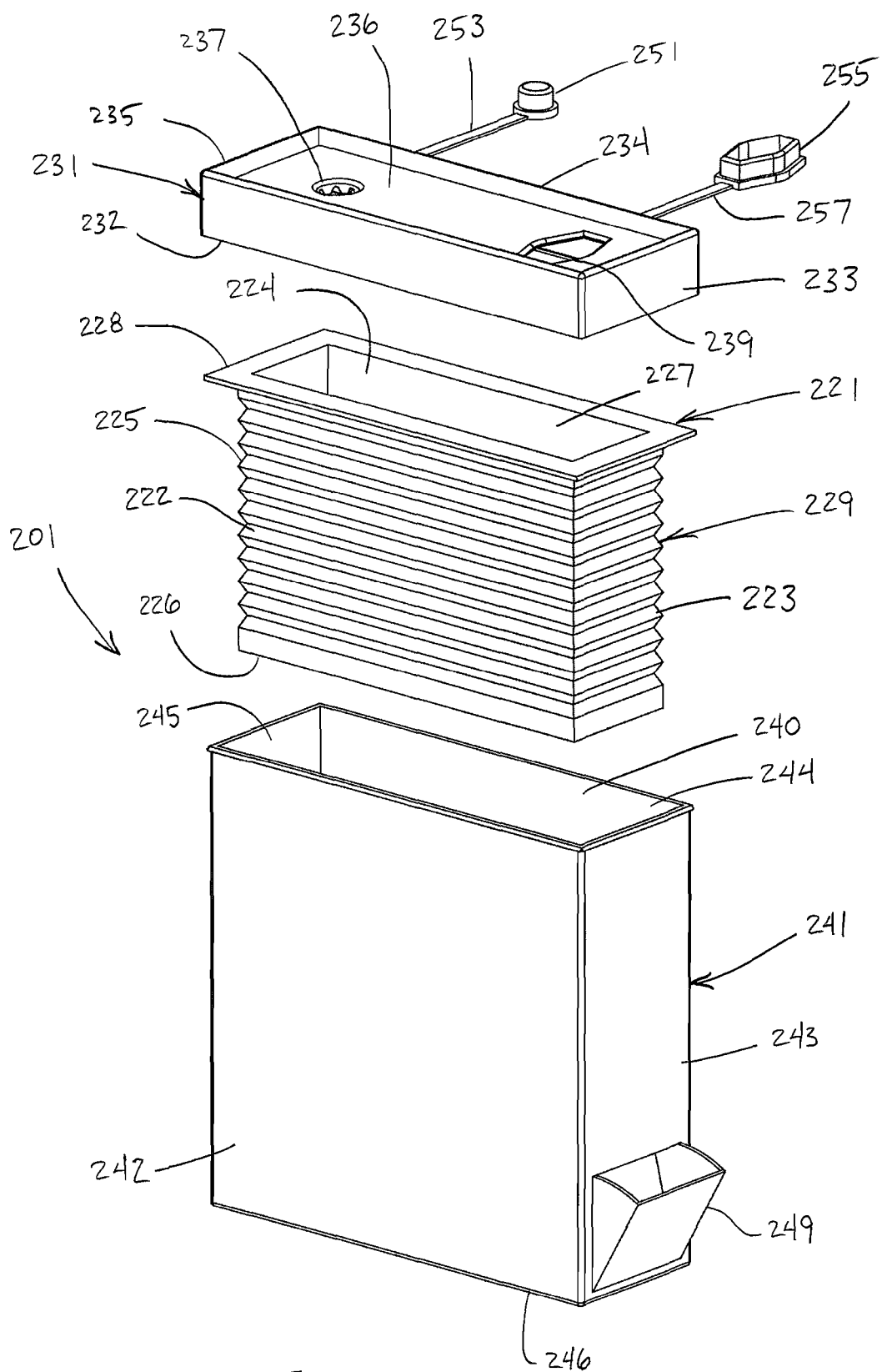
FIG. 7 is an exploded perspective view of a shipping container according to another exemplary embodiment of the present invention.

The lid 131 has side walls 132-135 extending substantially perpendicularly from a base 136. The lid 131 is adapted to be snap fit over either the bottom wall 126 of the sharps disposal container 121 for shipping as shown in FIG. 3, or over the open top of the sharps disposal container 121 in agreement with the side walls 122-125 thereof for receiving used sharps as shown in FIGS. 5 and 6. The lid 131 has an opening 137 in the base 136 through which used sharps are disposed to the internal volume 127 of the sharps disposal container 121. As shown in FIG. 7, a lid 231 may have a plurality of openings 237 and 239 of different sizes to accommodate a variety of used sharps.

The sharps disposal container 121 and the lid 131 are preferably made of made of a puncture-resistant plastic (polyethylene, polypropylene, polyethylene terephthalate, polylactide, or similar material).

When the shipping container 101 is ready to be shipped, the storage container 141 containing the new product is disposed within the sharps disposal container 121 and the lid 147 is closed, as shown in FIGS. 3 and 4. The lid 131 is snap fit over the bottom of the sharps disposal container 121. Thus, a shipping container 101 integrates a storage container 141 of new product 143 and a sharps disposal container 121, and is substantially the same size as the sharps disposal container 121.

When the shipping container 101 is received, the storage container 141 is removed from the sharps disposal container 121, and the top wall is pivoted away from the parallel position such that the new product stored therein is accessible. The storage container 141 may be stored in any convenient location, such as on a shelf, to access the stored new product 143 as needed. The lid 131 is removed from the bottom or the sharps disposal container 121 and connected to the top thereof, such as by a snap fit, as shown in FIGS. 5 and 6. Used sharps, such as a hub 20 and needle 11, may then be disposed of through the opening 137 in the lid to be stored in the internal volume 127 of the sharps disposal container 121. A hub-grabbing interface may be disposed in the opening 137, such as the pen needle sharps port disclosed in U.S. Pat. No. 7,021,463 to V. Phan, the entirety of which is hereby incorporated by reference. When the internal volume 127 of the sharps disposal container 121 is filled with used sharps, a plug (251 of FIG. 7) can be inserted in the opening 137 to provide a leak-proof container for the used sharps. Alternatively, a cover 151 (FIG. 6) may be disposed over the lid 131 to seal the sharps disposal container 121. The cover 151 is substantially similar to the lid 131 except that the lid does not have any openings to receive sharps. Preferably, the cover 151 is snap fit to the lid 131.

Figure 8:
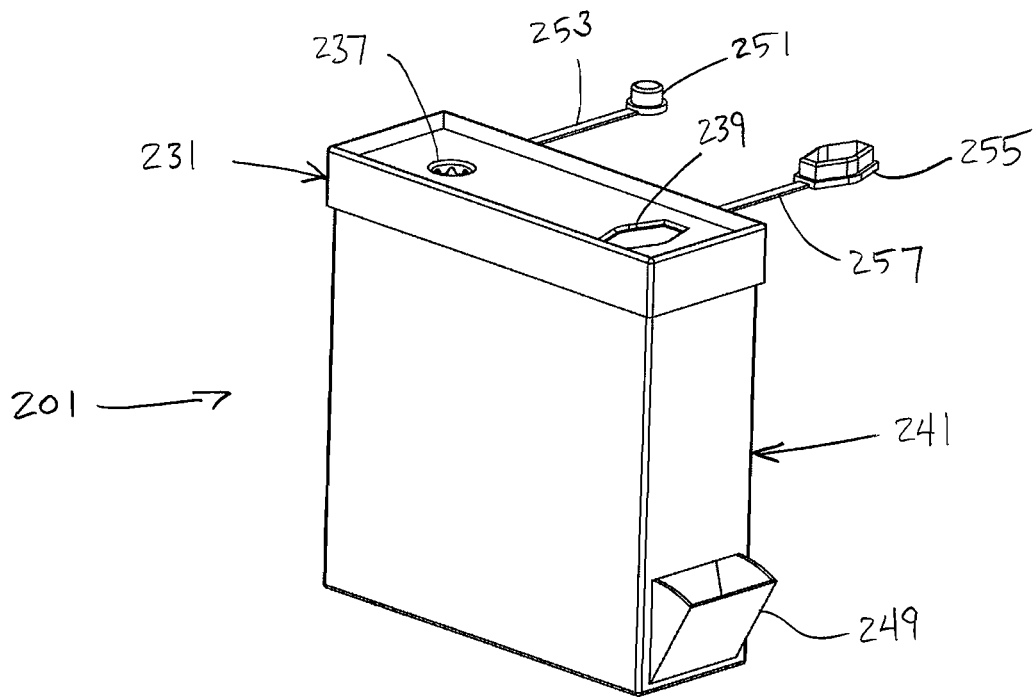
FIG. 8 is a perspective view of the assembled shipping container of FIG. 7.
Figure 9:
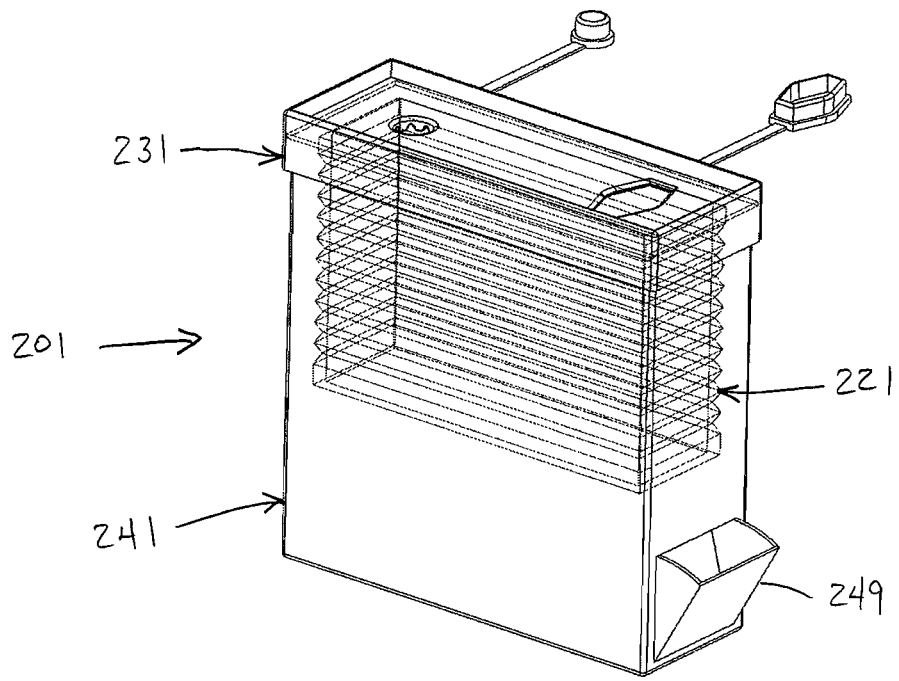
FIG. 9 is a perspective view of the assembled container of FIG. 8 in which the expandable sharps container is shown in phantom lines.

In another exemplary embodiment, as shown in FIGS. 7-9, the shipping container 201 has a new product storage container 241, a sharps disposal container 221 and a lid 231. The sharps disposal container 221 is disposed within the storage container 241, thereby creating a shipping container 201 that is substantially the same size as the storage container.

The storage container 241 contains new product, such as pen needle assemblies as shown in FIG. 4. The storage container 241 has side walls 242-245 extending upwardly and substantially perpendicularly from a bottom wall 246. The side walls 242-245 and the bottom wall 246 define an internal volume 240. A movable door 249 is formed in the side wall 243 to access the new product stored in the internal volume 240 of the storage container. In a closed position the door 249 is flush with the side wall 243. In an open position, access to the internal volume 240 is provided. The storage container 241 is preferably made of a puncture-resistant plastic (polyethylene, polypropylene, polyethylene terephthalate, polyactide or similar material). The new product is stored loose within the sealed storage container 241 between the bottom wall 246 of the storage container 241 and the bottom wall 226 of the sharps disposal container 221.

The sharps disposal container 221 has side walls 222-225 extending between a bottom wall 226 and a rim 228. The walls 222-226 define an internal volume 227 that is open at the top end and adapted to receive used sharps. The sharps disposal container 221 has a movable pleated or accordion-like portion 229 formed in the side walls 222-225 between the bottom wall 226 and the rim 228, thereby allowing the size of the sharps disposal container to be contracted or expanded. The movable portion 229 is contracted to reduce the size of the sharps disposal container 221, such as when empty for shipping in the new product storage container 241. The movable portion 229 allows the size of the sharps disposal container 221 to be expanded when receiving used sharps.

The lid 231 has side walls 232-235 extending substantially perpendicularly from a base 236. The lid 231 is adapted to be snap fit over storage container 241 and the sharps disposal container 221, or connected to the storage container 241 with the rim 228 disposed between the lid 231 and the storage container 241. Alternatively, the rim 228 of the sharps disposal container 221 may be ultrasonically welded to the underside of the lid 231. The lid 231 has an opening 237 in the base 236 through which used sharps are disposed to the internal volume 227 of the sharps disposal container 221. As shown in FIG. 7, the lid 231 may have a plurality of openings 237 and 239 of different sizes to accommodate a variety of used sharps. Plugs 251 and 255 may be integrally connected by flexible members 253 and 257, respectively, to the lid 231, thereby preventing misplacement and loss of the plugs.

The sharps disposal container 221 and the lid 231 are preferably made of made of a puncture-resistant plastic (polyethylene, polypropylene, polyethylene terephthalate, polylactide, or similar material).

When the shipping container 201 is ready to be shipped, the sharps disposal container 221 is disposed within the storage container 241 containing the new product and the lid 231 is connected to the storage container 241 as described above. The movable portion 229 of the sharps disposal container 221 is contracted to accommodate the new product stored in the storage container 241 in the area below the bottom wall 226 of the sharps disposal container 221. Thus, a shipping container 201 integrates a storage container 241 of new product and a sharps disposal container 221, and is substantially the same size as the storage container 241.

When the shipping container 201 is received, the door 249 of the storage container 241 is opened to access the new product stored in the storage container. Used sharps, such as a hub 20 and needle 11, may then be disposed through the opening 237 or 239 in the lid 231 to be stored in the internal volume 227 of the sharps disposal container 221. As more new product is removed from the internal volume 240 of the storage container 241, the movable portion 229 of the sharps disposal container 221 expands to fill the internal volume 240. The sharps disposal container 221 and lid 231 provide a stable, flexible and liquid-proof seal within the storage container 241.

When the internal volume 227 of the sharps disposal container 221 is filled with used sharps, a plug 251 can be inserted in the opening 237 to provide a leak-proof container for the used sharps. Alternatively, a cover 151 (FIG. 6) may be disposed over the lid 231 to seal the sharps disposal container 221.

By providing a shipping container that integrates a storage container for new product with a sharps disposal container for used product, with one of the storage and sharps disposal containers disposed in the other, the shipping container has substantially the same size as the larger of storage and sharps disposal containers.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims.

The invention claimed is:

1. A shipping container, comprising:
a storage container comprising a first top wall, a first bottom wall, and a first side wall defining a storage volume;
a disposal container comprising a second bottom wall and a second side wall defining a disposal volume, said storage container being disposed within said disposal container;
a lid adapted to be
removably attached to said second bottom wail of said disposal container, and
removably attached to said second side wall of said disposal container to further define said disposal volume,
said lid having an opening, said opening being positioned for receiving a used product into said disposal volume when said lid is attached to said second side wall of said disposal container; and
a plug to selectively seal said opening when said lid is attached to said second side wall of said disposal container to retain the used product inside said disposal volume of said disposal container.

2. The shipping container of claim 1, wherein
a size of said shipping container is substantially the same as a size as of the disposal container.

3. The shipping container of claim 1, wherein
at least one of said disposal container and said lid comprise puncture-resistant plastic.

4. The shipping container of claim 1, wherein
at least one of said disposal container and said lid comprise at least one of polyethylene, polypropylene or polylactide.

5. The shipping container of claim 1, wherein
a cover is selectively connected to said lid when said lid is attached to said second side wall of said disposal container to seal said disposal container.

6. The shipping container of claim 1, wherein
said lid has a plurality of different sized openings corresponding to different types of used product.

7. A shipping container, comprising:
a storage container comprising a first top wall, a first bottom wall, and a first side wall defining a storage volume;
a disposal container comprising a second bottom wall and a second side wall defining a disposal volume, said storage container being disposed within said disposal container;
a lid
removably attached to said second bottom wall of said disposal container, and
removably attached to said second side wall of said disposal container to further define said disposal volume,
said lid having an opening, said opening being positioned for receiving a used product into said disposal volume when said lid is attached to said second side wall of said disposal container; and
a cover selectively connected to said lid when said lid is attached to said second side wall of said disposal container to seal said disposal container.

8. The shipping container of claim 7, wherein
a size of said shipping container is substantially the same as a size of the disposal container.

9. The shipping container of claim 7, wherein
at least one of said disposal container and said comprise puncture-resistant plastic.

10. The shipping container of claim 7, wherein
at least one of said disposal container and said lid comprise at least one of polyethylene, polypropylene or polylactide.

11. The shipping container of claim 7, wherein
a plug selectively seals said opening when said lid is attached to said second side wall of said disposal container to retain the used product inside said disposal volume of said disposal container.

12. The shipping container of claim 7, wherein
said lid has a plurality of different sized openings corresponding to different types of used product.

* * * * *